United States Patent [19]
Seney

[11] Patent Number: 5,314,423
[45] Date of Patent: May 24, 1994

[54] COLD ELECTRODE PAIN ALLEVIATING TISSUE TREATMENT ASSEMBLY

[76] Inventor: John S. Seney, 57 Marlin Dr., Sugarloaf Shores, Fla. 33044

[21] Appl. No.: 970,850

[22] Filed: Nov. 3, 1992

[51] Int. Cl.⁵ ............................................. A61B 17/36
[52] U.S. Cl. ........................................ 606/20; 606/41; 607/46
[58] Field of Search ................................ 606/20–26, 606/32–35, 41, 42; 128/733–736, 399–403; 607/2, 3, 46

[56] References Cited
U.S. PATENT DOCUMENTS

| | | | |
|---|---|---|---|
| 3,270,744 | 9/1966 | Katz et al. | 606/25 |
| 4,140,109 | 2/1979 | Savic et al. | 606/21 |
| 4,207,897 | 6/1980 | Lloyd et al. | 606/23 |
| 4,860,744 | 8/1989 | Johnson et al. | 606/23 |

Primary Examiner—Stephen C. Pellegrino
Assistant Examiner—M. Peffley
Attorney, Agent, or Firm—Randy W. Lacasse

[57] ABSTRACT

A pain alleviating tissue treatment assembly uses a combination of a cold electrode and an alterable current source to reduce the temperature of a selected tissue area, while at the same time applying various selected reversing and/or non-reversing currents to the selected tissue. A control console allows the operator to selectively operate the device in conjunction with biological feedback signals and further allows full recordation and/or control of the events as they occur through an attached computer system.

44 Claims, 3 Drawing Sheets

COLD ELECTRODE PAIN ALLEVIATING TISSUE TREATMENT ASSEMBLY

BACKGROUND OF THE INVENTION

The present invention relates to a pain alleviating and tissue treatment assembly, and in particular, to a cold electrode assembly to alleviate pain and discomfort and accelerate healing in an transcutaneous electro neural stimulation process by reducing the temperature of the body tissues in contact with the cold current application electrode. This invention is also applicable to neuro surgery where small temperature controlled electrodes are implanted.

The nerves in the human body are associated with chemicals which combine and react according to an applied stimuli. Dependent upon this stimuli, a reaction results causing an electrical shift of the polarization of the neuron, or nerve, which then is transmitted as a pain signal or appropriate sensation. Because this reaction is basically chemical in nature, the reaction follows and obeys the general rule for stimuli activated reactions, and the reaction rate doubles for each 10° C. temperature increase. This acceptable principle has been used for years by surgeons and technicians in the medical profession by applying local anesthesia for minor surgery. Typically, compressed liquids such as ethyl chloride are sprayed directly on the tissue surrounding or involved in the surgical site. A substantial cooling of the tissue can result in an accompanying anesthetic effect. Some disadvantages are associated with this basic technique, including the requirement for the operator periodically to stop the treatment, and to recool the tissue surrounding the treatment site. Prior art patents include my own issued U.S. Pat. No. 4,646,735 for the PAIN ALLEVIATING TISSUE TREATMENT ASSEMBLY wherein a surgical site and the operating instrument are concurrently cooled to a substantially reduced temperature, using cold, dry, sterilized air gases or other treatment fluid. This assembly uses a liquid refrigerant and fluid system in combination with a microrefrigerating vaporator built into the handpiece, bringing cooling fluid to the working tip of the instrument and the site where the instrument is to be used.

The Deutsch U.S. Pat. No. 5,097,828 is a thermoelectrotherapy device using a heat sink for dissipating heat generated by Peltier effect devices. A contact plate is connected to a high voltage source to provide electrical stimulation to the skin and underlying tissue while applying the cold to the surface.

The Perler U.S. Pat. No. 4,614,191 discloses a skin cooling probe which anesthetizes, or desensitizes, a skin target area prior to removal of hairs by electrolysis. The cycle is limited to three seconds of cooldown followed by a twenty-five second heat sink cooling period, with this cycle repeated.

The Wong et al. U.S. Pat. No. 4,848,357, Morez U.S. Pat. No. 4,895,149, Rossen U.S. Pat. No. 4,989,605 and Slovak U.S. Pat. No. 5,058,605 are cited as being of general interest and relate to various non-invasive nerve stimulation devices in alleviating pain and treatment using an electrical energy system.

Other therapeutic devices of interest are shown in Tateisi U.S. Pat. No. 3,207,159, Kissen U.S. Pat. No. 4,585,002, Ghiurco et al. U.S. Pat. No. 4,860,748, Eidus U.S. Pat. No. 3,133,539, Okuhara U.S. Pat. No. 3,168,895, Ruderin U.S. Pat. No. 4,640,284 and Son U.S. Pat. No. 4,915,108. Patents for reducing the temperature of surgical instruments during the performance of surgical techniques are shown in Reynolds U.S. Pat. No. 3,548,829, Peters U.S. Pat. No. 3,494,364, Hershorn U.S. Pat. No. RE 26,276, Gregory U.S. Pat. No. 4,367,743, Kandbar U.S. Pat. No. 3,259,131, Zobac U.S. Pat. No. 4,345,598, Koloner U.S. Pat. No. 3,794,039 and Lloyd U.S. Pat. No. 4,207,897, among others.

Normal functioning of nerve and other body cells and tissue requires a very exact biochemical and biophysical composition and construct. The nervous system requirements are such that polarized electrical communication is almost instantly available from sensory to central decision making areas to motor and organ systems. Accidents, trauma, and disease processes frequently result in forces that apply stresses to individual nerve cells and aggregates, or bundles, of nerve cells and their parts. These stresses may cause ongoing, if not permanent, displacement of the nerve cells, their parts, and the biochemical components within and surrounding them. In some cases, the polarity of nerve fibers may be reversed, or perhaps merely reduced or neutralized. The unnatural conditions of polarity may alter the normal operation of the ion regulating channel in the presynaptic vesicles of a nerve transmitter mechanism, blocking the flow of sensory impulses to the sensory nervous system where decisions are made. They may occur in strategically placed locations that interfere with decision making or intelligence, or they may occur in areas that block motor messages being sent by the central nervous system to the end organs by way of the motor division of the nervous system.

In any of these situations, normal function of the total nervous system, and thus of the owner/vehicle of that nervous system is impaired. The impairment may manifest itself in the loss of sensation, such as pain, heat, cold and so forth. It may manifest itself as the inability to decide what to do or how to do it, as in some form of aplasia. It may show itself as an inability to move a body part, even though one knows precisely what one wants to do. It may mean that one loses an involuntary function, such as bladder control or the like.

One reason for reversed polarity is a forced transition of the biochemical organization of nerve cell composition where intracellular sodium, potassium and calcium ion control and generating sites are located. The function of these ion generating sites may be reversed or maladjusted. Nerve cells may be considered analogous to a pulse generating battery that has two plates with an electrolyte therebetween. The electrolyte has the ability to change ionic composition very rapidly in response to the activity at the plates. In this model, an overload or mechanical deviation might cause a positive cellular electrode or plate to become negative and/or a negative electrode or plate would become positive. If both plates or electrodes become the same polarity at the same time, no electrical pulse will be generated, and therefore it will not be recognizable or usable within the system. In this case, it would not be usable within the nervous system.

In many cases, scientifically manipulated mechanical and biogenerated electrical forces can be used to directly repolarize and/or urge disoriented nerves to become properly polarized. Even in cases where severe disorientation has occurred, the healing process can be significantly accelerated by including engineered electrophoric technology in the treatment process. This is done with transcutaneous electrical nerve stimulation devices, which are well known in the prior art.

This invention is capable of providing for the neurosurgeon small implantable electrodes that can be placed adjacent to or in the vicinity of damaged nerves or muscles. Small currents are applied in different selectable treatment modes while the electrode (positive or negative or both) is held at a substantially constant cold temperature.

SUMMARY OF THE INVENTION

The present invention is a closed loop feedback system to cool tissue to alleviate pain and accelerate healing using transcutaneous electro neural stimulation. The assembly of the invention reduces the temperature of the body tissues in contact with a cold current applicator electrode. The assembly having various control functions, a cold electrode which is placed on the area to be treated, a remote control biofeedback sensor which is applied to an area responsive to the treatment, and a body ground plate connected to a remote site on the patient to complete the electrical circuit. The cold treatment electrode cools the tissues over the area adjacent the effective nerves to a specific muscle group which are being treated to a tissue temperature that desensitizes the local sensory nerves at the treatment site to a level that will permit a comfortable healing treatment at a treatment power level that can result in forced neuro muscular action. Laboratory testing shows that by using the invention, the treatment level may be increased to approximately 8 times greater than the level which could be withstood without tissue cooling or some form of anesthesia. The hypothermic electrophoretic nerve treatment system of the present invention employs two electrodes. A large body grounding plate serves as one electrode. The cold treatment electrode has a very small skin contact area and produces a concentrated ionization force in that small area. The cold electrode lowers the temperature of the skin and connecting tissues approximately 60° below normal. The sensitivity of the nerves and mast cells that release pain, causing histamines, is therefore reduced by approximately 95%. This analgesic effect allows a higher ionization treatment current to be used that can penetrate deeper into the body mass with an energy level capable of moving ionized material by the proven electrophoretic process. Treatments at this level without cooling are too painful to be tolerated by the patient. The apparatus of the present invention is specifically designed to amplify the ionic treatment of nerves in order to enhance the healing capacity and return of normal function. The invention apparatus uses battery power and provides direct current nerve stimulating voltages that can be applied continuously or by alternating polarity and that are adjustable from 0 to 25 volts. The voltage is electronically generated and is variable in intensity for separate application modes. These application modes are manually selected by a switch on the control console.

DESCRIPTION OF THE PREFERRED EMBODIMENTS

Figure 1:
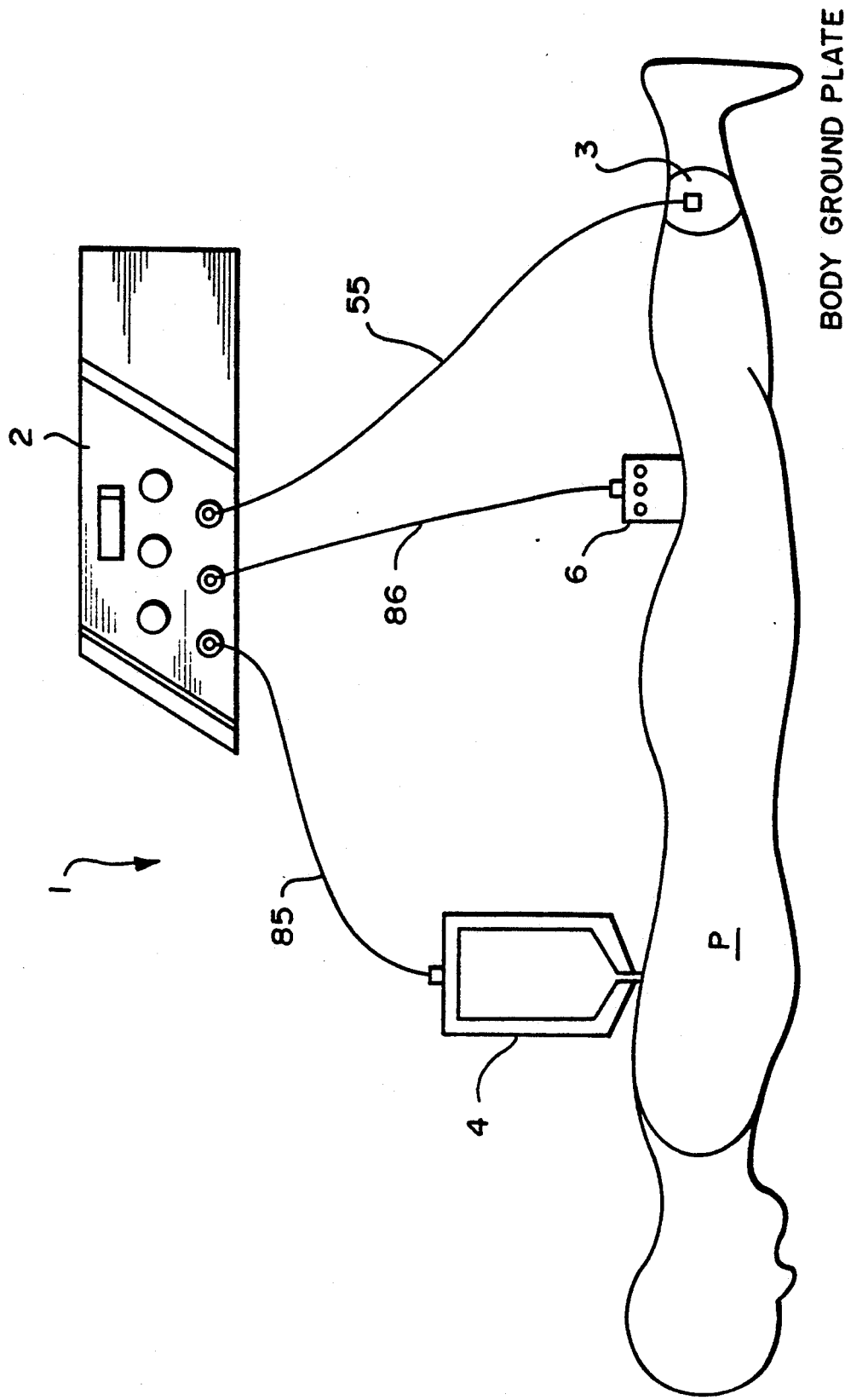
FIG. 1 is a diagrammatic view of the assembly of the present invention.

Referring to FIG. 1, a patient P lying in a prone position is being treated by the pain alleviating tissue treatment assembly 1 of the present invention. A control console 2, including the various control functions to be described hereinbelow in greater detail, is connected to a body grounding electrode 3, a cold electrode handpiece 4 and a remote control biofeedback assembly 6.

Figure 2:
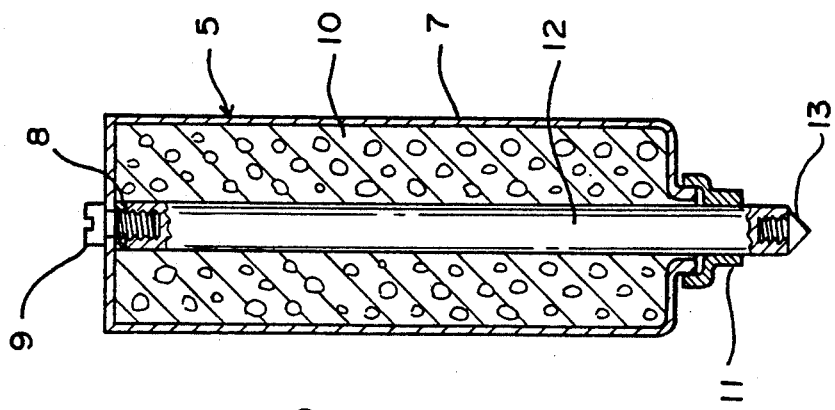
FIG. 2 is a sectional view of the cold electrode of the present invention.

Referring to FIG. 2, a cold electrode 5 is made with an outer aluminum canister 7 surrounding a cold electrode aluminum or copper rod 12. The rod is held in place by a retaining screw 9. A seal ring 8 is provided adjacent the retaining screw 9, and a silicone tubing electrode seal 11 is formed adjacent a stainless steel electrode tissue contact tip 13. The interior of the canister 7 contains a thermal storage fluid 10.

The aluminum canister 7 is approximately 1.4 inches (35 mm) in diameter and 3.9 inches (100 mm) long with a flat bottom and a conical top. The aluminum cold electrode rod preferably is of a 0.375 inch (10 mm) diameter and 4.675 inches (120 mm) long, tapped at both ends. The lower sealing ring 8 is preferably a neoprene gasket and as assembled on the lower end of the rod and seated against the lower inside canister bottom and secured by the retaining screw 9. The stainless steel tissue contact tip 13, in one embodiment, has a 45 degree tapered point and is screwed into the outer end of the rod 12. In other embodiments, the shape of this stainless steel tip may be changed to fit a specific medical application. The tip may vary in geometric shape to increase or decrease the actual skin contact area so that different degrees of concentrated ion flow may occur at the treatment site as required by the prescribed application. Further, these electrode tips may be implanted and take the form of micro patch clamp electrodes that can be attached to single neurons or muscle receptor points. The purpose of the stainless steel tip is to prevent galvanic transport of metal ions into the contacting tissues that possibly cause skin irritation. The canister is filled with 72 cc of thermal energy storage fluid, for example, Ethylene Glycol water solution, saline solution or equivalents. A tubular silicone sleeve 11 covers the rod 12 and the extension of the outer end of the canister. This type of seal will allow air and other trapped gases to escape, but acts as a check valve against outside gases trying to return to the inside of the canister as the fluid contracts to the liquid state.

Figure 3:
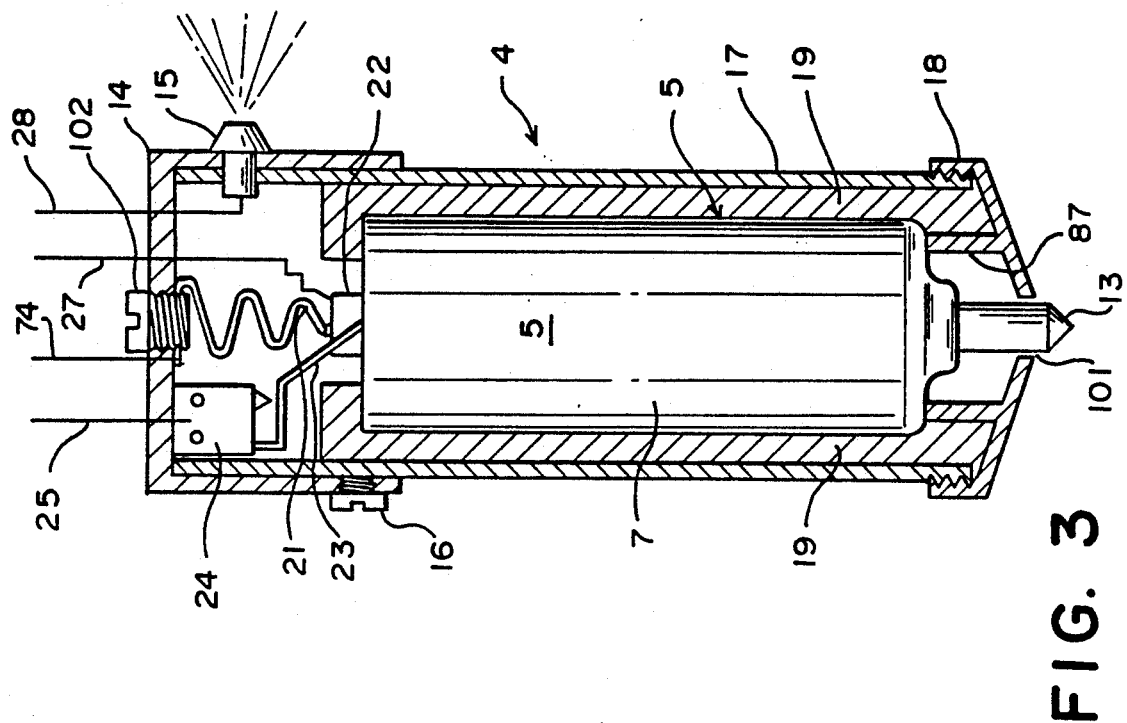
FIG. 3 is sectional view of the cold electrode in the cold electrode housing.

Referring to FIG. 3, the cold electrode 5 is placed in a cold electrode handpiece 4 formed of an outer handpiece threaded plastic housing 17, open at both ends, an end plate retainer 18 screwed on the lower open end and an upper end cap 14 secured by a cap retaining screw 16 to the upper open end. The handpiece 4 is designed to accommodate the cold electrode 5, but it will be appreciated that the size and shape may be changed for specific applications. An extended sleeve 87 acts as a forward movement stop for the cold electrode. The inward end of the sleeve 87 that touches the cold canister has three extending knife edged points (not shown) of contact to minimize thermal loss.

As can be seen from the drawing, the cold electrode 5 projects through an opening 101 in the retainer end plate 18 so that the tissue contact tip 13 projects outwardly from the cold electrode housing 4. Thermal insulation 19 is provided between the cold electrode canister 7 and the hand piece plastic housing 17. The endcap 14 includes a pilot light 15 which will be described hereinbelow. The housing 4 includes a temperature sensor 22 and a treatment time cycle start single pulse generator 24. A treatment switch trigger spring 23 is connected to the pulse generator to activate the electrode when it engages a patient as described hereinbelow. A contact spring 21 biases the cold electrode 5 toward the opposite open end of the housing 4. The contact spring 21 is held in place by a suitable screw 102, as shown. The overall size of the assembly has a diameter of approximately 2.25 inches (57 mm) and a length of 6.5 inches (166 mm). A four contact plug (not shown) is provided in the top of the handpiece 4 to connect it to the console 2 as described hereinbelow.

Figure 4:
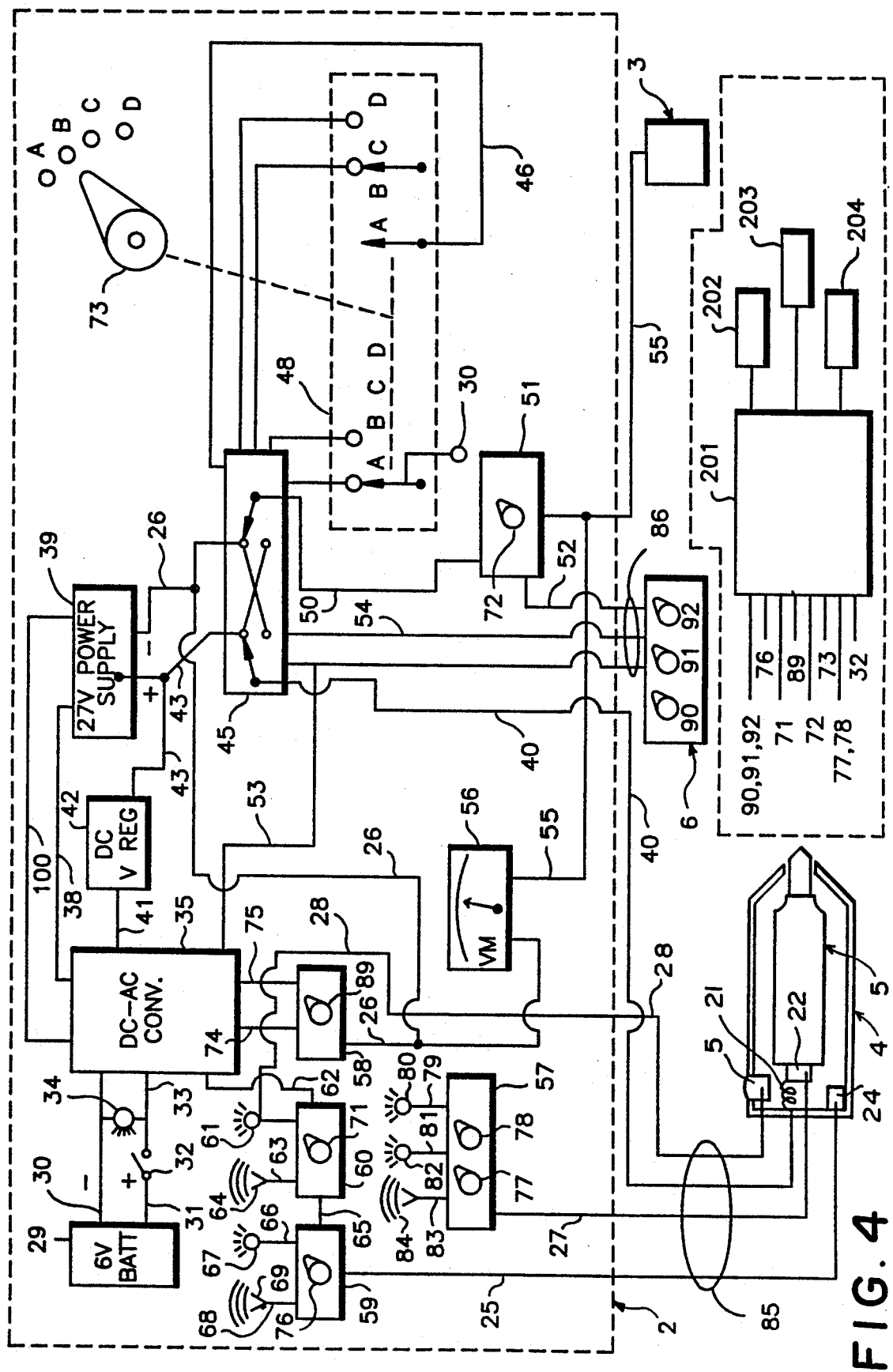
FIG. 4 is a block diagram of the system of the present invention.

Referring to FIG. 4, a block diagram of the entire system is shown. The body grounding electrode 3 is connected to the control console 2 using a connecting line 55. The remote control biofeedback assembly 6 is connected to the control console 2 through a remote control cable 86. The biofeedback assembly 6 includes an on/off control dial 90, a polarity reversal time control dial 91 and a treatment voltage control dial 92. The cold electrode 5 in the cold electrode handpiece 4 is connected to the control console 2 by cold electrode cable 85. The control console 2 includes a treatment mode selection switch 73 to select a particular treatment, as described hereinbelow.

Power to the system is supplied by a six volt lantern battery 29 connected to a DC to AC converter voltage supply unit 35 through a power "on/off" switch 32. A power "on/off" light 34 provides an indication that the battery is connected to and power is being supplied to the system. An output of the DC to AC converter voltage supply unit 35 is connected to a 27 volt positive power supply 39 through line 38 and common line 100. Output line 41 connects the DC to AC converter voltage supply unit 35 to a 27 volt DC regulator 42. A line 53 in cable 86 connects the remote control biofeedback assembly 6 to the "on/off" power circuits in the DC to AC converter voltage supply unit 35. A current limiter 58, having a treatment current control dial 89, is connected to the power circuits in the voltage supply unit 85 by lead 75 and a common lead 74. A volt meter 56 is connected between the line 26 and the body grounding electrode 3.

The control console 2 is provided with a cool cycle timer 59 having cool cycle timer adjusting control dial 76, an audible cool time alarm 69 and a "cool time" indicator lamp 67. A treatment cycle timer 60 having a time treatment adjustment control dial 71, an audible alarm 64, and an "on" treatment timer light 61. A high/low temperature alarm 57 includes low temperature alarm set point switch 77 and high temperature alarm set point switch 78. An audible temperature alarm 84 and low pilot light 82 and high pilot light 80 are also connected to the high/low temperature alarm 57. Line 62 connects the treatment cycle timer 60 and the cool cycle timer 59 to the DC to AC converter voltage supply unit 35. The treatment time cycle start single pulse generator 24 in the cold electrode housing assembly 5 is connected to the power circuits through timers 59 and 60.

The high/low temperature alarm unit 57 is connected directly to the temperature sensor 22 on the cold electrode 5 through line 27. The high/low temperature alarm 57 includes a low temperature alarm set point dial 77 and a high temperature alarm set point dial 78. A high temperature pilot light 80, a low temperature pilot light 82 and an audible temperature alarm 84 are provided with the high/low temperature alarm unit 57.

Various contacts of the treatment mode selection switch 73 are connected to different control inputs of the electronic switch 45, depending on the treatment mode selected, as described hereinbelow.

The output of the positive power supply 39 is connected to an electronic double pole double throw polarity reversal switch 45 which is connected to the treatment mode switch contacts 48. A voltage control 51 is connected between one of the common switch contacts 50 and the body grounding electrode 3 and the remote control biofeedback assembly 6, the voltage control 51 includes a treatment adjustment dial 72.

The remote control biofeedback assembly 6 provides a feedback control signal to the treatment program, which can alter the treatment current voltage and polarity applied to the cold electrode 5. A biofeedback sensor (not shown) has provisions for several different input sensors, including treatment time, muscle tension, muscle motion, muscle generated voltages, muscle position, skeletal joint position, bioelectrical nerve output, programmed skeletal position and nerve stimulation current with positive feedback and also operation by the patient to either draw pressure or pneumatically through the patient's breath. The biofeedback assembly includes an "on/off" control switch 90, a polarity reversal time control dial 91, and a treatment voltage control dial 92 to adjust the feedback signals.

All manually operated treatment functions shown in FIG. 4 (elements 32, 71, 72, 73, 76, 77, 78, 89, 90, 91 and 92) can be operated by a plug-in computer controller 201 which is programmable by keyboard 202. Input and output treatment events are recorded on printer 203 with a permanent record recorded on floppy disk 204 or an equivalent digitized memory recorder. Recorded events may include, but are not limited to:

1. Power on/off to treatment system
2. Time and date
3. Patient name and address
4. Patient symptoms and degree of discomfort prior to treatment on a scale of 1 to 10
5. Skeletal joint identification and degrees of movement prior to treatment
6. Muscle tone prior to treatment
7. Treatment electrode body position
8. Cool down time (sec)
9. Treatment time (sec)
10. Treatment voltage (volts)
11. Treatment current level (micro amps)
12. Skin irritation at treatment electrode contact points
13. Cold (treatment) electrode temperature
14. Degree of improvement on scale of 1 to 10
15. Skeletal joint movement after treatment (degrees)
16. Triggered muscle action during treatment application
17. Patient comments
18. Doctor comments and other pertinent information
19. Vascular/capillary blood flow improvement The general operation of the pain alleviating tissue treatment assembly may be described as follows. The invention is capable of reducing the temperature of tissue in contact with the cold electrode to a specific controllable level from 98° F. to below 27° F. by controlling one of the following specific parameters: tissue contact area of the cold electrode, tissue contact pressure of the cold electrode, tissue application time of the cold electrode and steady state temperature of the cold electrode.

The hand held cold electrode handpiece is flexibly coupled to the control console by means of the cable 85. The cold electrode contact spring 21, located on the inside end of the electrode handpiece, electrically connects the cold electrode to the treatment control circuits in the console 2. An adjustable treatment sequential two-step timer 24 is triggered by the treatment switch trigger spring 23 and starts the treatment cycle once the cold electrode 5 is pressed against the skin of a patient. This causes the cold electrode 5 to make a slight inward movement, as the electrode is pressed against the treatment site. This action initiates the first stage of the sequential timer 59 located in the control console 2. A green pilot light 67 and recognizable audible tone generator 69 are turned on by the timer 59, indicating that the cool down period is progressing. The treatment cycle timer 60 is automatically triggered on at the end of the cool down period. The treatment on time is adjustable to suit the treatment period. During treatment, cold is continually applied as well. The two red pilot lights 61 of the treatment cycle timer 60 and the light 15 of the cold electrode handpiece 4, plus an audible sound generator 64 provide visual and audible signals that the treatment current is being applied for this time period.

Four types of treatment output currents are generated in the console, plus remote control modification to regulate the treatment and application in all of these modes. The adjustable current limits the output treatment currents flowing through the cold electrode 5 from 10 to a maximum of 800 microamperes, and can be applied in all modes of operation. The output voltage is indicated on a meter 56, having a scale between 0-25 volts. The voltage will be automatically reduced to a level controlled by the current limit set point. Treatment Mode 1 uses a direct current with a 20 Hz reversing rate. Treatment Mode 2 uses direct current with a 6 Hz reversing rate. Treatment Mode 3 uses a direct current which is non-reversing, with the cold electrode positive and the body grounding electrode negative. Treatment Mode 4 is non-reversing, with the cold electrode negative and the body grounding electrode positive.

FIG. 1 shows a patient being treated for a spinal problem using the cold electrode handpiece 4 applied to the tissue in the spinal area, causing treatment current to flow into the spine and through the body grounding electrode attached to the patient's leg. The remote control feedback sensor assembly 6 is placed over a muscle affected by the nerves being stimulated, and it modifies the treatment current in response to a change in muscle tension. This is a closed-loop feedback system, and the stimulated nerve and its associated muscle can be recycled and exercised, promoting regeneration of the damaged neuro muscular system and preventing atrophy until full function is restored by repeated treatments. The cold treatment electrode 5 cools the tissue over the small area above the affected nerves to a specific muscle group to a tissue temperature that desensitizes the local sensory nerves at the treatment site to a level that will permit a comfortable healing treatment at a treatment power level that can affect forced neuro muscular action. The duration of the cool down cycle timer is controlled by adjustment knob 76. Initially, the cool timer 59 is adjusted to a preset value, for example, 20 seconds. The treatment cycle timer 60 controls the treatment time. The duration of the treatment time is adjusted with the treatment timer dial 71 adjusted to a treatment time, for example, 25 seconds. The treatment voltage is set to a predetermined value, as indicated by the voltmeter 56, using dial 72 on the output voltage control unit 51. The current limit control dial 89 is preset to a specific current level, for example, 25 microamperes.

Normally, the cold electrode is kept refrigerated to maintain it at a frozen temperature. When treatment begins, the cold electrode 5 is taken from the refrigerator and installed inside the handpiece 4. The power switch 32, in the "on" position, connects the battery 29 to the DC to AC converter voltage supply unit 35. The contact of the cold treatment electrode against the skin of a patient at the treatment site causes the cold electrode to make a slight inward movement, which connects the cold electrode contact spring 21 with the one-shot timer trigger switch 24, sending a trigger pulse through line 25 to the cool timer. The hand pressure on the handpiece not only compresses the cold electrode contact spring switch, but also maintains a constant electrode pressure against the tissue. In order for the hypothermic anesthesia to take place in the tissues of the treatment site, adequate cooling time must be provided to cool the tissue mass to the required anesthetized level prior to the application of the treatment current. The pulse turns the cool timer 59 on, along with the cool time green pilot light 67 and the audible generator 69. The cool timer 59 provides a cool down time adjust, which is adjustable from 10 to 30 seconds, and is set to provide adequate cooling to a point where the treatment current is not uncomfortable to the patient. At the end of the preset cool time period, both the pilot light 67 and the tone generator 69 go off. At the same instant, a treatment time start pulse is generated by the timer 59 and sent through line 65 to the treatment timer 60. The treatment timer 60 is adjustable to regulate the time of the treatment period. This time start pulse turns on the red treatment time pilot light 61 and the red pilot light 15 in the handpiece 4, and also activates the treatment time audible tone generator 61. A treatment voltage "on" signal is also sent by way of line 62 to turn on the high voltage converter that converts the 6 volt battery voltage to 50 volts, 70 KHz AC. Lead 38 feeds a positive 27 volt DC supply 39.

The output of the direct current 27 volt supply is connected to a DC voltage regulator 42. Line 43 is positive and line 26 is negative. The output of the 27 volt DC supply 39 is connected to the electronic polarity reversing switch 45. The polarity of the output switch 45 will either be positive or negative, depending upon its position, and therefore the voltage between the common line 40 and the output lead 46 of the switch 45 will have a polarity depending upon switch position. The electronic switch 45 has two built in cycle rates plus constant output in either polarity and provision for remote control operation. The normal rate is 20 Hz, when the polarity selection dial 73 on the console 2 is in a first position. When the switch 73 is in a second position, the cycle rate control line 49 is connected to line 30 through the switch 48, which changes the polarity reversing rate to 6 Hz. The line 50 provides 27 volts positive or negative output in all treatment modes into the treatment voltage control 51. Line 55 feeds the adjusted voltage to the body grounding plate 3, and to one terminal of the output volt meter 56. The other terminal of the volt meter connects to the common line 40, which in turn is connected to the cold treatment electrode 5.

There are four modes of treatment voltages, plus modifications that can be effected by the remote control sensors 6, applied to the patient. These are selected by the position of the electric dial 73 on the control console 2. Previously, it was shown that when the dial 73 is in the "A" position, the polarity reversal is 20 Hz. With the dial in the "B" position, the polarity reversal is 6 Hz. In position "C", a voltage is applied to switch 45 via line 44 that positions switch 39 to its lower position, connecting the body contact plate 3 to the positive terminal of power supply 39 and the cold electrode terminal 40 to the negative terminal of power supply 39. In position "D", the switch 45 position is thrown to the upper position via a signal from line 36. This reverses the polarity of body grounding plate 3 and the cold electrodes. These connections allow continuous, non-reversing DC treatment voltages.

If the dial is in the "C" position, the body contacting electrode polarity will be positive, and the cold electrode will be negative. If the dial 73 is placed in the "D" position, the cold electrode will be positive in a body electrode negative. The lead 74 leaves a high voltage DC to AC converter voltage supply unit 35 and connects to the current limiting controller 58. Line 26 leaving the limit controller 58 attaches to the voltmeter 56 and to the negative output terminal of the DC power supply. The current controller output control signal line 75 connects to the current control circuits in the DC to AC converter voltage supply unit 35.

In a second mode of operation, biofeedback is provided to the healing process to exercise and heal damaged neuro muscular groups. In this case, the same general standard equipment settings are used. The cold electrode is used to search and find the area that causes muscle action. The treatment voltage and current reversal frequency is adjusted for consistent muscular response for a given stimulus current. The cold electrode is then clamped in a holding fixture at the proper treatment site. The remote control biofeedback assembly, which senses muscle tension, is already entered over the muscle for maximum output voltage, which may be monitored on an oscilloscope (not shown). The signal is adjusted by "on/off" control dial 90 through line 53 to the output voltage control circuits in the DC to AC converter voltage supply unit 35 and provides "on/off" control in response to the muscle action. Muscle action produces a specific sensed output voltage wave form, starting with the first muscle contraction force instigated by the application of the treatment voltage into the cold electrode 5. As time progresses, the output voltage sensed by the feedback sensors' assembly 6 also rises with time. The polarity reversal time control dial 91 on sensors 6 selects the time period after the muscle has reacted and the selected period fires a control pulse by way of line 54 into the polarity switch that reverses the treatment polarity, allowing the muscle to relax. The sensors' assembly 6 fires a control pulse through line 54 that reverses the position of the polarity reversing switch 45. This, in turn, causes the muscle to contract. This process continues to cycle for the duration of the treatment period. The treatment voltage control dial 92 on the sensor assembly 6 is used to control the treatment voltage level through line 52 to the voltage control 51.

I claim:

1. A non-invasive tissue treatment device providing cooling and electrical stimulation comprising:
    a removable cold electrode comprising:
        an external metallic housing;
        an internal electrical conduit;
        a thermal storage fluid encapsulated between said external housing and said conduit, and
    a gasket interconnecting said external housing and said conduit;
    an insulative housing for holding said removable cold electrode;
    a control console operatively coupled to said insulative housing and said cold electrode for providing an alterable electrical source to said electrode and control thereof;
    a biofeedback device comprising at least one sensor for providing biological data to said control console, and
    wherein said removable cold electrode is brought into contact with said tissue and said alterable electrical source is transferred thereto.

2. A non-invasive tissue treatment device as per claim 1, wherein said housing has an opening and said electrical conduit extends beyond said housing through said opening.

3. A non-invasive tissue treatment device as per claim 2, wherein said electrical conduit has an interchangeable tip depending upon the desired medical application.

4. A non-invasive tissue treatment device as per claim 1, wherein said insulative housing comprises:
    an external housing;
    an insulative material contained therein;
    a cavity formed within said insulative material for encapsulating said removable cold electrode;
    an electrical source; and,
    a connector means for selectively connecting said cold electrode to said electrical source.

5. A non-invasive tissue treatment device as per claim 4, wherein said insulative housing further comprises a tension biased member, which when compressed, enables said connector means to make said removable cold electrode connection to said electrical source.

6. A non-invasive tissue treatment device as per claim 4, wherein said insulative housing further comprises a visual indicator for indicating said connection to said electrical source.

7. A non-invasive tissue treatment device as per claim 4, wherein said insulative housing has an opening and said removable cold electrode extends partially beyond said insulative housing.

8. A non-invasive tissue treatment device as per claim 1, wherein said feedback assembly device is remotely coupled to said control console.

9. A non-invasive tissue treatment device as per claim 1, wherein said feedback assembly device further comprises a polarity reversing controller and a voltage controller.

10. A non-invasive tissue treatment device as per claim 1, further comprising a grounding electrode operatively coupled to said control console.

11. A non-invasive tissue treatment device a per claim 1, further comprising a computer controller/recording means operatively coupled to said control console.

12. A non-invasive tissue treatment device as per claim 1, wherein said control console comprises:
    a power source;

a voltage supply source connected to said power source;

a current limiting means;

at least one application cycle timing means; and, a polarity reversing means operatively coupled to said voltage supply source.

13. A non-invasive tissue treatment device as per claim 12, wherein said control console further comprises:

a visual alarm means; and, an audible alarm means.

14. A non-invasive tissue treatment device as per claim 12, wherein said power source is a battery.

15. A non-invasive tissue treatment device as per claim 12, wherein said voltage power source provides for regulated positive and negative voltage sources.

16. A non-invasive tissue treatment device as per claim 12, wherein said at least one application cycle timing means comprises at least a cooling cycle timer and a treatment cycle timer.

17. A non-invasive tissue treatment device as per claim 12, wherein said polarity reversing means provides for a plurality of different reversing and non-reversing output currents.

18. A non-invasive tissue treatment device providing cooling and electrical stimulation comprising:

a removable cold electrode comprising:

an external metallic housing;

an internal electrical conduit;

a thermal storage fluid encapsulated between said external housing and said conduit, and a gasket interconnecting said external housing and said conduit;

an insulative housing for holding said cold electrode;

a control console connected to said insulative housing and said removable cold electrode for providing an alterable electrical source to said electrode and control thereof;

a biofeedback device comprising at least one sensor for providing biological data to said control console and, a grounding electrode operatively connected to said control console.

wherein said removable cold electrode is brought into contact with said tissue and said alterable electrical source is transferred thereto.

19. A non-invasive tissue treatment device as per claim 18, wherein said external housing is metallic to allow thermal and electrical conduction and has an opening with said electrical conduit extending beyond said housing through said opening.

20. A non-invasive tissue treatment device as per claim 18, wherein said insulative housing comprises:

an external housing;

an insulative material contained therein;

a cavity formed within said insulative material for encapsulating said removable cold electrode;

an electrical source; and, a connector means for selectively connecting said removable cold electrode to said electrical source.

21. A non-invasive tissue treatment device as per claim 20, wherein said insulative housing further comprises a tension biased member which when compressed enables said connector means to make said cold electrode connection to said electrical source.

22. A non-invasive tissue treatment device as per claim 20, wherein said insulative housing further comprises a visual indicator for indicating said connection to said electrical source.

23. A non-invasive tissue treatment device as per claim 20, wherein said insulative housing has an opening and said cold electrode extends partially beyond said insulative housing.

24. A non-invasive tissue treatment device as per claim 18, wherein said feedback assembly further comprises a polarity reversing controller and a voltage controller.

25. A non-invasive tissue treatment device as per claim 18, further comprising a computer controller/recording means operatively connected to said control console.

26. A non-invasive tissue treatment device as per claim 18, wherein said control console comprises:

a power source;

a voltage supply source connected to said power source;

a current limiting means;

at least one application cycle timing means; and, a polarity reversing means connected to said voltage supply source.

27. A non-invasive tissue treatment device as per claim 26, wherein said voltage power source provides for regulated positive and negative voltage sources.

28. A non-invasive tissue treatment device as per claim 26, wherein said polarity reversing means provides for a plurality of different reversing and non-reversing output currents.

29. A non-invasive tissue treatment device as per claim 26, wherein said control console further comprises:

a visual and audible alarm means;

at least a cooling cycle timer and a treatment cycle timer; and, a temperature sensing means.

30. A non-invasive tissue treatment device providing cooling and electrical stimulation comprising:

a removable cold electrode;

an insulative housing for substantially encapsulating said removable cold electrode; and, a control console operatively coupled to said insulative housing and said cold removable electrode comprising:

a regulated positive and negative voltage source;

a plurality of reversing and non-reversing output current sources;

a temperature sensing means;

at least a cooling cycle and treatment cycle timer;

a biofeedback device comprising at least one sensor for providing biological data to said control console;

a grounding electrode operatively coupled to said control console;

a computer controller operatively coupled to said control console for recording and/or controlling the operation of said tissue treatment device, and wherein said removable cold electrode is brought into contact with said tissue and said alterable electrical source is transferred thereto.

31. A non-invasive tissue treatment device as per claim 30, wherein said removable cold electrode comprises:

an external housing;

an internal electrical conduit;

a thermal storage fluid encapsulated between said external housing and said conduit; and, a gasket interconnecting said external housing and said conduit.

32. A non-invasive tissue treatment device as per claim 31, wherein said external housing is metallic to allow thermal and electrical conduction and has an opening with said electrical conduit extending beyond said housing through said opening.

33. A non-invasive tissue treatment device as per claim 30, wherein said insulative housing comprises:
an external housing;
an insulative material contained therein;
a cavity formed within said insulative material for encapsulating said removable cold electrode;
an electrical source; and,
a connector means for selectively connecting said removable cold electrode to said electrical source.

34. A non-invasive tissue treatment device as per claim 33, wherein said insulative housing further comprises:
a tension biased member, which when compressed, enables said connector means to make said removable cold electrode connection to said electrical source;
a visual indicator for indicating said connection to said electrical source; and,
a temperature sensor.

35. A non-invasive tissue treatment device as per claim 2, wherein said feedback device further comprises a polarity reversing controller and a voltage controller.

36. A non-invasive tissue treatment device a per claim 30, wherein said control console further comprises:
a power source;
a voltage supply source connected to said power source;
a current limiting means;
at least one timing means;
a polarity reversing means connected to said voltage supply source; and,
visual and audible alarms.

37. A non-invasive tissue treatment device providing cooling and electrical stimulation comprising:
a removable cold electrode;
a thermal storage fluid contained within said removable cold electrode;
an insulative housing for substantially encapsulating said removable cold electrode;
a control console operatively coupled to said insulative housing and said removable cold electrode comprising:
a regulated positive and negative voltage source;
a plurality of reversing and non-reversing output current sources;
a temperature sensing means;
at least a cooling cycle and treatment cycle timer;
a pressure sensitive switch coupling said output current sources to said removable cold electrode through said insulative housing;
a biofeedback device comprising at least one sensor for providing biological data to said control console;
a grounding electrode operatively coupled to said control console;
a computer controller operatively coupled to said control console for recording and/or controlling the operation of said tissue treatment device, and
wherein said removable cold electrode is brought into contact with said tissue and said plurality of reversing and non-reversing output current sources are transferred thereto.

38. A non-invasive tissue treatment device as per claim 37, wherein said removable cold electrode comprises:
an metallic external housing;
an internal electrical conduit extending partially beyond said external housing;
and wherein said thermal storage fluid is encapsulated between said external housing and said conduit; and,
a gasket interconnecting said external housing and said conduit.

39. A non-invasive tissue treatment device as per claim 37, wherein said insulative housing comprises:
an external housing;
an insulative material contained therein, and
a cavity formed within said insulative material for encapsulating said removable cold electrode.

40. A non-invasive tissue treatment device as per claim 37, wherein said pressure sensitive switch comprises:
a tension biased member, which when compressed, enables a connector means to make said removable cold electrode connection to said electrical source;
a visual indicator for indicating said connection to said electrical source; and,
a temperature sensor.

41. A non-invasive tissue treatment device as per claim 37, wherein said biofeedback device further comprises a polarity reversing controller and a voltage controller.

42. A non-invasive tissue treatment device as per claim 37, wherein said control console further comprises:
a power source;
a voltage supply source connected to said power source;
a current limiting means;
at least one timing means;
a polarity reversing means connected to said voltage supply source; and,
visual and audible alarms.

43. A method for the alleviation of pain with the combination of a reduction in associated tissue temperature and simultaneous electrical stimulation to said associated tissue, said method comprising:
cooling of a cold electrode to a frozen temperature;
insertion of said frozen cold electrode into an insulative handpiece;
selectively coupling said insulative handpiece containing said electrode to an alterable and variable current source; and,
operatively coupling said current source to a feedback sensing means whereby contacting of said cold electrode to said tissue in combination with said alterable and variable current source in conjunction with said feedback sensing means provides for the alleviation of pain.

44. A method for the alleviation of pain with the combination of a reduction in associated tissue temperature and simultaneous electrical stimulation to said associated tissue, said method comprising:
cooling of a cold electrode to a frozen temperature;
insertion of said frozen cold electrode into an insulative handpiece;

selectively coupling said insulative handpiece containing said electrode to an alterable and variable current source; and, operatively coupling said current source to a feedback sensing means;

recording and/or controlling the operational parameters of said cold electrode, said current source and said feedback sensing means, and whereby contacting of said cold electrode to said tissue in combination with said alterable and variable current source in conjunction with said feedback sensing means provides for the alleviation of pain.

* * * * *